United States Patent [19]

Giles et al.

[11] Patent Number: 5,147,885

[45] Date of Patent: Sep. 15, 1992

[54] N-AMINO BICYCLIC COMPOUNDS

[75] Inventors: Heather Giles; Alan D. Robertson; Michael G. Kelly; Leff, Paul, all of Beckenham, England

[73] Assignee: Burroughs Wellcome Co., Research Triangel Park, N.C.

[21] Appl. No.: 704,436

[22] Filed: May 23, 1991

[30] Foreign Application Priority Data

May 24, 1990 [GB] United Kingdom ............... 9011589

[51] Int. Cl.$^5$ .................. A61K 31/415; A61K 31/41; C07D 235/02; C07D 257/04
[52] U.S. Cl. .................................. 514/381; 514/382; 514/387; 514/339; 548/253; 548/302
[58] Field of Search ............... 548/302, 253; 514/381, 514/382, 387

[56] References Cited

U.S. PATENT DOCUMENTS 4,432,988  2/1984  Harris et al. ................... 548/302
4,537,972  8/1985  Harris et al. ................... 548/302

FOREIGN PATENT DOCUMENTS 0046597  3/1982  European Pat. Off. .
2098214  11/1982  United Kingdom .

Primary Examiner—Joseph P. Brust
Assistant Examiner—M. S. H. Gabilan
Attorney, Agent, or Firm—Nixon & Vanderhye

[57] ABSTRACT

N-amino hexahydrocyclopenta imidazole-2(1H)-one derivatives useful for treating or preventing thromboembolic disorders and ocular diseases characterized by increased ocular pressure.

9 Claims, No Drawings

N-AMINO BICYCLIC COMPOUNDS

This invention is concerned with a novel class of N-amino hexahydrocyclopenta[d]imidazole-2(1H)-one derivatives. The preparation of these compounds, medicaments containing them and their use as therapeutic agents are also within the scope of the invention.

In EP-A-0046597, there are described certain diazabicyclooctanedione derivatives which have pharmacological properties related to those of natural prostaglandins, as demonstrated by their ability to mimic or antagonise the physiological effects of the natural prostaglandins in various biological preparations.

We have now discovered a novel class of N-amino hexahydrocyclopenta[d]imidazole-2(1H)-one derivatives having particularly advantageous pharmacological properties arising from their improved selectivity for the $PGD_2$-class of receptors over other prostanoid receptor types, thereby increasing potency at this class of receptor. Such selectivity finds application in the treatment and prophylaxis of conditions in which this class of receptor is implicated, for example, blood platelet aggregation and increased intraocular pressure.

According to a first aspect of the present invention, therefore, there is provided a compound of formula (I):

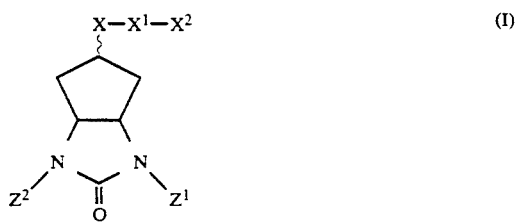

wherein:
X represents a sulphur atom or oxygen atom or a group $—NR^1—$ or $—CR^1R^2—$, in the alpha- or beta-configuration, where $R^1$ and $R^2$ are hydrogen or straight or branched $C_{1-5}$ alkyl;

$X^1$ represents a $C_{1-5}$ straight chain or branched alkylene group, a $C_{3-5}$ straight chain or branched alkenylene group or a substituted or unsubstituted $C_6$ or $C_{10}$ aromatic group, the optional substituents on the aromatic group being one or more of $C_{1-4}$ alkyl, $C_{1-4}$ alkoxy, nitro, halo and trihalomethyl;

$X^2$ represents a cyano, carboxyl, carboxamide, hydroxymethyl, $C_{2-5}$ alkoxycarbonyl, or 5-tetrazolyl group;

$Z^1$ represents a group selected from $—NH—CH_2—R^3$ and $—N=CH—R^3$ wherein $R^3$ is a group selected from $—CO—Y$ and $—CH(Y^1)Y$, Y being a group selected from $C_{3-8}$ alkyl, $C_{3-8}$ alkenyl, phenyl-$C_{1-4}$ alkyl and phenyl (wherein the phenyl group in both cases is optionally substituted by one or more groups independently selected from $C_{1-4}$ alkyl, $C_{1-4}$ alkoxy, nitro, halo and trihalomethyl), cycloalkyl of from 4 to 8 carbon atoms and 5- and 6-membered heterocyclic radicals containing at least one oxygen, sulphur, or nitrogen heteroatom and $Y^1$ being a group selected from hydroxy, hydrogen, $C_{1-4}$ alkoxy and $C_{1-5}$ alkanoyloxy;

$Z^2$ represents hydrogen, $C_{1-12}$ alkyl (straight or branched), $C_{2-12}$ alkenyl or alkynyl, $C_6$ or $C_{10}$ aryl or $C_6$ or $C_{10}$ aryl-$C_{1-12}$ alkyl wherein the aryl group is optionally substituted by one or more groups independently selected from phenyl, $C_{1-4}$ alkyl, $C_{1-4}$ alkoxy, nitro, halo and trihalomethyl) or cycloalkyl of from 3 to 5 carbon atoms;

and salts, esters and other physiologically functional derivatives thereof.

The term "physiologically functional derivatives" includes, for example, amides of the compounds of formula (I) and bioprecursors or "pro-drugs" of said compounds which are converted in vivo to compounds of formula (I) and/or their salts or derivatives. Solvates, for example, hydrates, of the compounds of formula (I) and of their salts, esters and physiologically functional derivatives are also within the scope of the present invention.

Preferred compounds of formula (I), by virtue of their advantageous pharmacological properties, include those wherein X represents a sulphur atom, an oxygen atom, or a methylene group in the beta-configuration;

$X^1$ represents a $C_{3-4}$ straight alkyl chain;

$X^2$ is a carboxy group or a corresponding $C_{1-4}$ alkyl ester or salt thereof;

$Z^1$ is a group selected from $—NH—CH_2—R$ wherein R is a group of formula $—CH(Y^1)Y$ in which $Y^1$ is hydroxy and Y is phenyl, alkyl of from 3 to 8 carbon atoms, or cycloalkyl of from 4 to 8, particularly 6, carbon atoms; and $Z^2$ is a group selected from hydrogen, $C_{1-6}$ straight and branched alkyl and $C_3-C_6$ cycloalkyl, especially ethyl and propyl.

The most preferred compound of formula (I) for the treatment of thrombo-embolic disorders is 5-(3-carboxypropylthio)-1-(2-cyclohexyl-2-hydroxyethylideneamino)-3-ethylhexahydrocyclopenta[d]imidazol-2(1H)-one. For the treatment of ocular diseases, two of the most preferred compounds of formula (I) are 5-(3-carboxypropylthio)-1-(2-cyclohexyl-2-hydroxyethylideneamino)hexahydrocyclopenta[d]imidazol-2-(1H)-one and 5-(3-carboxypropylthio)-1-(2-cyclohexyl-2-hydroxyethylamino)hexa-hydrocyclopenta[d]imidazol-2(1H)-one.

Particularly valuable salts for medical purposes are those having a pharmaceutically acceptable cation, such as an alkali metal, for example, sodium and potassium, an alkaline earth metal, for example, calcium and magnesium, ammonium, or an organic base, particularly an amine, such as ethanolamine. Salts having non-pharmaceutically acceptable cations are within the scope of this invention as useful intermediates for the preparation of pharmaceutically acceptable salts and derivatives or for use in non-therapeutic applications, for example, in vitro or ex vitro prostanoid receptor differentiation.

When Y is a five- or six-membered heterocyclic radical as defined above, the ring of the radical may be saturated or unsaturated. Examples include pyridyl, thienyl, tetrahydropyranyl and tetrahydrofuryl.

Except when there is a clear indication to the contrary, formula (I) and other formulae in this specification embrace all stereoisomers represented therein. In particular, such formulae include the enantiomeric forms, racemates and diastereomers.

As indicated, the compounds of formula (I) are of value in having pharmacological properties related to those of natural prostaglandins. Thus, the compounds may mimic or antagonise the effects of members of the prostaglandin D series. For example, compounds of formula (I) have been found to mimic the anti-aggregatory effects of PGD$_2$ on blood platelets and reduce intraocular pressure.

Compounds of formula (I) have advantages over the 2,4-diazabicyclo[3.3.0.]octane-3,7-dione derivatives disclosed in EP-A-0046597 in that they demonstrate substantially improved selectivity for the DP-class of receptors over other prostanoid receptor types and markedly greater potency at the DP-class of receptor. It follows that these compounds demonstrate a greater therapeutic index than the 2,4-diazabicyclo[3.3.0.]octane-3,7-dione derivatives of EP-A-0046597 as blood platelet anti-aggregatory agents and agents for the reduction of intraocular pressure.

According to a second aspect of the invention, therefore, there is provided a compound of formula (I) for use in a method of treatment of the human or animal body by therapy, particularly the treatment of prophylaxis of a thrombo-embolic disorder or a condition giving rise to increased intraocular pressure, for example, glaucoma. By the term "thrombo-embolic disorder" is meant a disorder whose aetiology is associated with blood platelet aggregation.

The compounds of the invention are particularly useful in the treatment and prevention of myocardial infarction, thromboses and strokes. The compounds may also be used to promote the potency of vascular grafts following surgery and to treat complications of arteriosclerosis and conditions such as atherosclerosis, blood clotting defects due to lipidaemia and other clinical conditions in which the underlying aetiology is associated with lipid imbalance or hyperlipidaemia. A further use for these compounds is as an additive to blood and other fluids which are used in artificial extracorporeal circulation and the perfusion of isolated body portions. The compounds of formula (I) and their salts and derivatives may also be used in the treatment of peripheral vascular disease and angina and, as indicated, in the treatment of ocular diseases, particularly those which give rise to increased intraocular pressure, for example, glaucoma.

According to a third aspect of the invention, there are provided methods for the prophylaxis or treatment of a thrombo-embolic disorder in a mammal and for the prophylaxis or treatment of a condition giving rise to increased intraocular pressure in a mammal which comprise administering to said mammal a therapeutically effective amount of a compound of formula (I) or of a salt, ester, or other physiologically functional derivative.

Hereinafter the term "a compound of formula (I)" includes salts, esters and other physiologically functional derivatives of said compounds and solvates of all thereof.

The amount of a compound of formula (I) required to achieve the desired biological effect will depend on a number of factors, for example, the specific compound chosen, the use for which it is intended, the mode of administration and the general condition of the recipient. In general, a daily dose may be expected to lie in the range of from 0.1 mcg to 20 mg per kilogram bodyweight. For example, an intravenous dose may lie in the range of from 5 mcg or 10 mcg to 1 mg/kg which may conveniently be administered as an infusion of from 0.01 to 50 mcg per kilogram per minute. Infusion fluids suitable for this purpose may contain from 0.001 to 100, for example, from 0.01 to 10, mcg per millilitre, preferably 1 to 10 mcg/ml. Unit doses may contain from 10 mcg to 100 mg, for example, ampoules for injection may contain from 0.01 to 1 mg and orally administrable unit dose formulations, such as tablets or capsules, may contain from 0.1 to 50, for example, 2 to 20 mg. Such dosage units may be administered, for example, 1, 2, 3 or 4 times per day, separately or in multiples thereof.

More specifically, when a compound of formula (I) is used to inhibit platelet aggregation it is generally desirable to achieve a concentration in the appropriate liquid, whether it be the blood of a patient or a perfusion fluid, of about 1 mcg to 10 mg, for example, from 10 mcg to 1 mg, per litre. For opthalmic applications, a concentration in the range 0.04 g/L to 10 g/L is generally preferred.

According to a fourth aspect of the invention, there are provided pharmaceutical formulations comprising, as active ingredient, at least one compound of formula (I) together with at least one pharmaceutical carrier. The carrier must, of course, be 'acceptable' in the sense of being compatible with the other ingredients of the formulation and not deleterious to the recipient. The carrier may be a solid or a liquid and is preferably formulated with a compound of formula (I) as a unit dose formulation, for example, a tablet, which may contain from 0.05% to 95% by weight of the active ingredient. Other pharmacologically active substances may also be present in the formulations of the present invention, for example, when treating a thrombo-embolic disorder, a beta-adrenoceptor blocking agent, such as propranolol, or when treating intraocular pressure, a muscarinic agonist, such as pilocarpine, or a beta-antagonist, such as timolol.

According to a fifth aspect of the invention, there is provided a method of preparing a medicament which comprises admixing a compound of formula (I) with a pharmaceutically acceptable carrier. The formulations may be prepared by any of the well-known techniques of pharmacy consisting essentially of admixing the components of the formulation.

Formulations according to the invention include those suitable for oral, buccal (e.g. sub-lingual), parenteral (e.g. subcutaneous, intramuscular, intradermal and intravenous) and topical (e.g. opthalmic) administration, although the most suitable route in any given case will depend in the nature and severity of the condition being treated and on the nature of the active compound.

Formulations suitable for oral administration may be presented as discrete units such as capsules, cachets, lozenges, or tablets each containing a predetermined amount of the active compound; as powders or granules; as solutions or suspensions in aqueous or non-aqueous liquids; or as oil-in-water or water-in-oil emulsions. Such formulations may be prepared by any of the methods of pharmacy, all of which include the step of bringing into association the active ingredient with the carrier which comprises one or more appropriate ingredients. In general, the formulations of the invention may be prepared by uniformly and intimately admixing the active ingredient with liquids or finely divided solid carriers, or both, and then, if necessary, shaping the product into the desired presentation. For example, a tablet may be prepared by compression or moulding a powder or granules of the active ingredient, optionally with one or more accessory ingredients. Compressed tablets may be prepared by compressing the active ingredient in a free-flowing form, such as a powder or granules optionally mixed with a binder, lubricant, inert diluent and/or surface-active or dispersing agent(s). Moulded tablets may be made by moulding the powdered active ingredient moistened with an inert liquid diluent in a suitable machine.

Formulations suitable for buccal (e.g. sub-lingual) administration include lozenges comprising the active ingredient in a flavoured base, e.g. sucrose and acacia or tragacanth, and pastilles comprising the active ingredient in an inert base such as gelatin and glycerin or sucrose and acacia.

Formulations suitable for parenteral administration conveniently comprise sterile aqueous preparations of the active ingredient, which preparations are preferably isotonic with the blood of the recipient. The preparations are preferably administered intravenously, although administration may be effected by means of subcutaneous or intramuscular injection. Such preparations may conveniently be prepared by admixing the active ingredient with water and rendering the product sterile and isotonic with the blood.

Topical formulations are particularly suitable for opthalmic use and preferably take the form of an ointment, cream, lotion, paste, gel, spray, aerosol, or oil. Carriers which may be used in such formulations include petroleum jelly, lanolin, polyethylene glycols, alcohols and combinations thereof. The active ingredient is generally present at a concentration of from 0.1 to 15% w/w of the composition, for example, from about 0.5 to about 2% w/w.

As indicated, by reason of their prostaglandin DP-receptor properties, the compounds of formula (I) may be used in the pharmacological characterisation and differentiation of the biological activities of the natural prostaglandins and their receptors.

According to a sixth aspect of the invention, there is provided the use of a compound of formula (I) in the manufacture of a medicament for the treatment or prophylaxis of a thrombo-embolic disorder or of a condition giving rise to increased intraocular pressure.

The compounds of formula (I) may be prepared in any conventional manner, for example, by the method described below. According to a seventh aspect of the invention, therefore, there is provided a process for the preparation of compounds of formula (I) which comprises:

reacting a compound of formula (II)

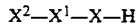

$$X^2-X^1-X-H \qquad (II)$$

wherein X, $X^1$ and $X^2$ are as hereinbefore defined, or functional equivalents thereof, with a compound of formula (III)

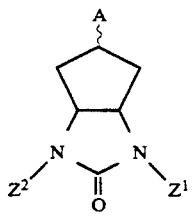

(III)

wherein $Z^1$ and $Z^2$ are as hereinbefore defined and A is a suitable leaving group in the alpha- or beta-configuration, in the presence of a base, such as an alkali metal alkoxide;

and optionally converting the compound of formula (I) so obtained to another compound of formula (I) or to a salt, ester, or other physiologically functional derivative of either.

The leaving group A may be a mesylate, tosylate, halogen, or any other suitable group.

The compound of formula (II) may conveniently be employed in the form of a salt, viz

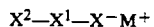

$$X^2-X^1-X^-M^+$$

wherein $M^+$ is an alkali metal cation, for example, sodium. The use of two equivalents of the compound of formula (II) per equivalent of the compound of formula (I) avoids the necessity for subsequent base treatment.

When using the above process to prepare a compound of formula (I) in which group X is in the alpha-configuration, a compound of formula (III) in which the leaving group A is in the beta-configuration should be used. Similarly, to prepare a compound of formula (I) in which X is in the alpha-configuration, a starting material of formula (III) in which the leaving group A is in the beta-configuration is required. The latter starting materials may be prepared from corresponding starting materials of formula (III) containing a different leaving group in the beta-configuration by reacting the latter material with a suitable reagent serving to replace the first leaving group (in the beta-configuration) with a second (desired) leaving group (also in the beta-configuration). Thus, for example, a compound of formula (III) in which A represents a halogen atom in the beta-configuration may be prepared by reaction of a corresponding compound of formula (III) in which A represents a hydrocarbonsulphonyloxy group in the beta-configuration with an appropriate source of halide anions, for example, an alkali metal halide, such as lithium chloride.

A compound of formula (III) wherein A represents a leaving group in the alpha- or beta-configuration may be prepared by reacting a compound of formula (IV)

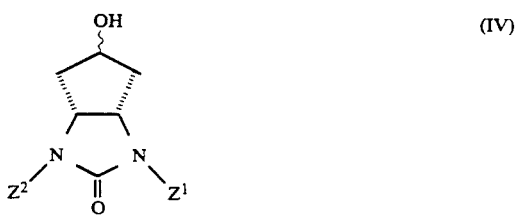

(IV)

wherein $Z^2$ and $Z^1$ are as hereinbefore defined and the hydroxyl group is in the alpha- or beta-configuration, with an appropriate reagent serving to introduce the group A in the same configuration. Thus, for example, a compound of formula (IV) may be reacted with a hydrocarbonsulphonyl halide, for example, a chloride, to introduce a hydrocarbonsulphonyl group. The reaction is conveniently effected in the presence of an organic base, such as pyridine.

A compound of formula (IV) wherein the hydroxy group is in the beta-configuration can be prepared from a compound of formula (IV) wherein the hydroxy group is in the alpha-configuration by inversion, for example, using triphenylphosphine and diethylazodicarboxylate, following the method of Mitsunobu (*Tetrahedron Lett.* (1972) 1279).

A compound of formula (IV) where $Z^1$ and $Z^2$ are as already defined can be prepared by reacting a compound of formula (V)

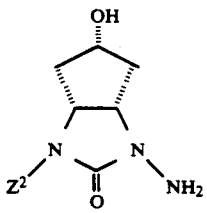

wherein $Z^2$ is a hereinbefore defined, with a compound

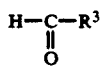

wherein $R^3$ is as hereinbefore defined, in the presence of a base in an appropriate solvent, for example, methanol.

A compound of formula (V) where $Z^2$ is as hereinbefore defined may be prepared by reducing a compound of formula (VI)

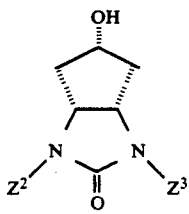

wherein $Z^2$ is as defined and $Z^3$ can be $Z^1$ as hereinbefore defined or an alternative imino protecting group, for example, benzylideneimino —N=CH—Ph, using a suitable reducing system, such as catalytic hydrogenation.

A compound of formula (IV) may be prepared by reacting a compound of formula (VII)

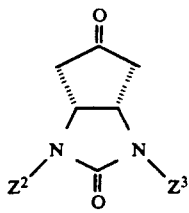

wherein $Z^2$ and $Z^3$ are as hereinbefore defined, with an appropriate reducing agent such as a metal hydride, sodium borohydride being particularly suitable for this purpose.

Compounds of formula (VII) may be prepared from a compound of formula (VIII)

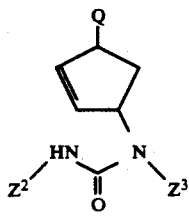

wherein Q represents a carbonyl or carbonyl-protecting group, for example, an ethylenedioxy group, by cyclisation under acid or base conditions. When acidic conditions are used, the reaction conveniently results in deprotection of the carbonyl group and concomitant cyclisation of the heterocyclic ring. When basic conditions are used for the cyclisation, a carbonyl-protecting group, if present, has to be removed in a prior step under acid conditions.

Compounds of formula (VIII) may be prepared by reacting a compound of formula (IX)

wherein Q and $Z^3$ are as hereinbefore defined, with cyanic acid or a $Z^2$-substituted isocyanate or, alternatively, by reaction with phosgene or its equivalent and subsequent treatment with an appropriate $Z^2$-substituted amine, wherein $Z^2$ is as hereinbefore defined.

Compounds of formula (IX) may be prepared by reacting a compound of formula (X) with a compound of formula (XI)

wherein Q and $Z^3$ are as hereinbefore defined and B is a leaving group, preferably bromine, in the presence of a base, such as pyridine, in a suitable, preferably non-protic, solvent, such as toluene.

Compounds of formula (X) may be prepared from cyclopent-2-enone in a conventional manner, for example, according to the method of DePuy (*J. Org. Chem.* 28, 3508 (1964)) in the case of the preparation of 5-bromo-3,3-ethylenedioxycyclopentene.

The invention also provides novel intermediates of formulae (II) to (X).

The following Examples illustrate the invention.

SYNTHETIC EXAMPLES

EXAMPLE 1

Preparation of 5-(3-Methoxycarbonylpropylthio)-1-(2-cyclohexyl-2-hydroxyethylideneamino)-3-propyl-hexahydrocyclopenta[d]imidazol-2(1H)-one (a) Cyclopentenone ethyleneketal Cyclopentenone ethyleneketal was prepared from cyclopentanone, ethylene glycol and bromine followed by subsequent dehydrohalogenation by literature methods: see E. W. Garbisch, *J. Org. Chem.*, 30, 2109 (1965).

(b) 5-Bromo-3,3-ethylenedioxycyclopentene

5-Bromo-3,3-ethylenedioxycyclopentene was prepared from the compound of step (a) by the method of DePuy (*J. Org. Chem.*, 29, 3508 (1964)).

(c) Benzaldehyde 1,4-dioxaspiro[4.4]non-6-en-8-ylhydrazone

The allylic bromide of step (b) (0.178 mol) was dissolved in toluene (50 ml) and the solution cooled to −40° C. with stirring. Benzaldehyde hydrazone (0.141 mol) in toluene (50 ml) was added rapidly over 5 minutes, followed by triethylamine (25 g). The solution was warmed slowly to 15° C. and stirred at this temperature for 16 hours. The mixture was then brought to a gentle reflux for a further 5 hours. After cooling, the triethylamine hydrobromide formed was filtered off under reduced pressure and the resulting solution concentrated in vacuo and purified by chromatography (silica, diethyl ether). This gave the desired product as an oil (18.9 g).

(d) Benzaldehyde 2-(1,4-dioxaspiro[4.4]non-6-en-8-yl)-4-propylsemicarbazone

The compound of step (c) (16 g) and pyridine (12.25 g) were added to toluene (300 ml) and the resulting solution cooled to 0° C. To this stirred mixture, a solution of phosgene in toluene (12.5%, 125 ml) was rapidly added over 10 minutes, after which the solution was warmed to 15° C. and stirred for a further 20 minutes. n-Propylamine (20 ml) was added to the solution at 0° C. over 5 minutes and, after stirring for a further 30 minutes, water (200 ml) was added. The organic layer was separated and dried over anhy. sodium sulphate. After filtration, concentration in vacuo gave the desired product as a brown gum (21.0 g).

(e) 1-Benzylideneamino-3-propyltetrahydrocyclopenta[d]imidazol-2,5(1H,3H)-dione An acetone solution (150 ml) of the compound of step (d) (21 g) was stirred at 15° C. while camphorsulphonic acid (2.5 g) was added portionwise over 10 minutes. After 4 hours, the mixture was concentrated in vacuo, water (150 ml) and chloroform (100 ml) added and the organic phase separated. The latter was washed with dilute sodium bicarbonate (100 ml), separated and concentrated in vacuo to give the desired product as a brown oil (21.0 g).

(f) 1-Benzylideneamino-3-propyl-5-hydroxyhexahydrocylopenta[d]imidazol-2(1H)-one The compound of step (e) (21 g) was dissolved in methanol (100 ml) and the solution cooled to 0° C. while sodium borohydride (1.5 g) was added portionwise over 15 minutes. When addition was complete, the solvent was removed in vacuo, water (100 ml) and chloroform (100 ml) added and the organic phase separated. After drying over anhy. sodium sulphate, filtration and concentration in vacuo gave the crude product as a brown gum (21 g). This was purified by column chromatography (silica, 10:1 diethyl ether:methanol) to give the desired product as fine white needles (7.5 g), mp 150.3°–150.8° C.

% C 66.97 % H 6.96 % N 14.59

$^1$H NMR: (CDCl$_3$, δ) 7.8 (1H, s, N=C$\underline{H}$), 7.7–7.2 (5H, m, Ph), 4.4 (1H, m, C$\underline{H}$N), 4.2 (1H, m, C$\underline{H}$OH), 3.5 (1H, m, CH of CH$_2$N), 3.05 (1H, m, CH of C$\underline{H}_2$N), 0.9 (3H, t, CH$_3$)

(g) 1-amino-3-propyl-5-hydroxyhexahydrocyclopenta[d]imidazole-2(1H)-one

The compound of step (f) (7.0 g) was added to a solution of methanol (280 ml) and acetic acid (2.25 ml) containing 10% Pd on carbon (2.5 g) and the resulting mixture stirred at 15° C. under an atmosphere of hydrogen for 3 days. The catalyst was removed by filtration through Celite and concentration of the filtrate in vacuo gave the desired product as an oil (5.0 g).

(h) 5-Hydroxy-1-(2-cyclohexyl-2-acetoxyethylideneamino)-3-propylhexahydrocyclopenta[d]imidazole-2(1H)-one A solution of the compound of step (g) (5.0 g) and 2-acetoxy-2-cyclohexylacetaldehyde (Ross et al, J. Med. Chem., 22, 412 (1979), 6.0 g) in methanol (175 ml) containing sodium acetate (3.64 g) was stirred at 15° C. under a nitrogen atmosphere for 16 hours. The alcohol was removed in vacuo and water (100 ml) and chloroform (100 ml) added. The organic phase was separated and washed with brine (100 ml), then dried over anhy. sodium sulphate. Filtration and concentration of the filtrate in vacuo gave a yellow oil (10.8 g).

Column chromatography of the crude product (silica, 7% methanol in diethyl ether) gave the desired produced as a pair of diastereoisomers (7.8 g).

(i) 5-Methanesulphonyloxy-1-(2-cyclohexyl-2-acetoxyethylideneamino)-3-propylhexahydrocyclopenta[d]imidazole-2(1H)-one To a solution of the compound of step (h) (7.8 g) and pyridine (3.6 g) in dichloromethane (100 ml) at 0° C. under an atmosphere of nitrogen was added methanesulphonyl chloride (5.2 g). After stirring for 20 hours, water (100 ml) was added and the organic layer separated. The latter was washed with 1N HCl (100 ml) and again separated and dried over anhy. magnesium sulphate. Filtration and concentration of the filtrate in vacuo gave 10.0 g of crude product containing both diastereoisomers.

The individual diastereoisomers, compound A and compound B, were separated by column chromatography (silica, 3% methanol in ethyl acetate).

Less polar isomer: Compound A: 3.0 g
More polar isomer: Compound B: 3.1 g $^1$H NMR (CDCl$_3$, δ): Compound A: 7.15 (1H, d, N=C$\underline{H}$), 5.05 (1H, m, C$\underline{H}$OMs), 4.9 (1H, t, C$\underline{H}$OAc), 4.20 (1H, dd, C$\underline{H}$N), 4.0 (1H, dd, C$\underline{H}$N), 2.70 (3H, s, SO$_2$C$\underline{H}_3$), 1.85 (3H, s, COCH$_3$)

(j) 5-(3-Methoxycarbonylpropylthio)-1-(2-cyclohexyl-2-hydroxyethylideneamino)-3-propylhexahydrocyclopenta[d]imidazol-2(1H)-one Under an atmosphere of nitrogen, thiobutyrolactone (1.72 g) was added to methanolic sodium methoxide (from sodium, 390 mg) in dry methanol (20 ml)) at 15° C. and the resulting solution stirred for two hours. The solvent was removed in vacuo and the residue dissolved in dry dimethylsulphoxide (20 ml) under nitrogen.

Compound A of step (i) (3.0 g) in dimethylsulphoxide (10 ml) was added in one portion to the thiolate solution and the resulting mixture stirred at 15° C. for 16 hours. The solution was diluted with water (200 ml) and the crude product extracted into diethyl ether (200 ml). After drying over anhy. sodium sulphate, the mixture was filtered and the filtrate concentrated in vacuo to give an oil. Column chromatography (silica, 5% methanol in ethyl acetate) gave the desired product as a colourless oil (1.4 g).

$^1$H NMR (CDCl$_3$, δ): 7.2 (1H, d, N=C$\underline{H}$), 4.25 (1H, dd, C$\underline{H}$N), 4.1 (1H, dd, C$\underline{H}$N), 4.0 (1H, m, $\underline{C}$HOH), 3.55 (3H, s, CO$_2$C$\underline{H}_3$), 0.80 (3$\underline{H}$, t, C$\underline{H}_3$)

EXAMPLE 2

5-(3-Carboxypropylthio)-1-(2-cyclohexyl-2-hydroxyethylideneamino)-3-propylhexahydrocyclopenta[d]imidazol-2(1H)-one The compound of Example 1 (1.4 g) was dissolved in methanol:water (2:1, 10 ml) and to the stirred solution was added lithium hydroxide (0.267 g). The resulting mixture was maintained at 45° C. for one hour. The pH was adjusted to 5.0 with 2N HCl, water (50 ml) was added and the product was extracted into chloroform (50 ml). After drying over anhy. sodium sulphate, the mixture was filtered and the filtrate concentrated in vacuo to give the desired product (1.15 g).

$^1$H NMR (CDCl$_3$, δ): 7.2 (1H, d, N=C$\underline{H}$), 4.4 (1H, dd, C$\underline{H}$N), 4.2 (1H, dd, C$\underline{H}$), 4.1 (1H, m, $\underline{C}$HOH), 0.9 (3H, t, C$\underline{H}_3$)

EXAMPLE 3

5-(3-Carboxypropylthio)-1-(2-cyclohexyl-2-hydroxyethylamino)-3-propylhexahydrocyclopenta[d]imidazol-2(1H)-one The compound (0.5 g) of Example 2 was dissolved in a mixture of methanol (5 ml) and acetic acid (5 ml) at 15° C. and to the stirred solution was added sodium cyanoborohydride (0.15 g). After one hour, the solution was concentrated in vacuo, water (20 ml) and chloroform (20 ml) were added and the organic phase separated and dried over anhy. sodium sulphate. Filtration and concentration of the filtrate in vacuo gave the desired produced (0.49 g).

$^1$H NMR (CDCl$_3$, δ): 4.1 (2H, m, 2×C$\underline{H}$N), 3.2 (1H, m, C$\underline{H}$OH), 0.9 (3H, t, C$\underline{H}_3$)

EXAMPLE 4

5-(3-Methoxycarbonylpropylthio)-1-(2-cyclohexyl-2-hydroxyethylideneamino)-3-ethylhexahydrocyclopenta[d]imidazol-2(1H)-one This compound was prepared following the general procedure of Example 1, except that in step (d) ethylamine was used instead of n-propylamine. In addition to this compound, compounds which correspond respectively to the compound of step (f) and compound A except that they are 3-ethyl rather than 3-propyl were prepared and subjected to NMR analysis:

5-(3-Methoxycarbonylpropylthio)-1-(2-cyclohexyl-2-hydroxyethylideneamino)-3-ethylhexahydrocyclopenta[d]imidazol-2(1H)-one $^1$H NMR (CDCl$_3$, δ): 7.4–7.2 (2H, m, C$\underline{H}$=N and O$\underline{H}$), 4.6–4.1 (3H, m, NC$\underline{H}$CHN and C$\underline{H}$OH), 3.9–3.4 (4$\underline{H}$, m, CO$_2$C$\underline{H}_3$ and C$\underline{H}_2$N*), 3.4–2.8 (2$\underline{H}$, m, C$\underline{H}_2$N* and SC$\underline{H}$), 2.8–2.1 (6H, m, SC$\underline{H}_2$CH$_2$CH$_2$CO$_2$), 2.1–1.0 (18H, m, remaining protons)

1-Benzylideneamino-3-ethyl-5-hydroxyhexahydrocyclopenta[d]imidazol-2(1H)-one $^1$H NMR (CDCl$_3$, δ): 7.8 (1H, d, C$\underline{H}$=N), 7.7–7.3 (5H, m, Ph), 4.5–4.4 (2H, m, NCHC$\underline{H}$N), 4.3–4.1 (1H, m, C$\underline{H}$OH), 3.8–3.5 (1H, m, C$\underline{H}_2$N*), 3.3–3.0 (1H, m, CH$_2$N*), 2.3–1.9 (4H, m, 2×C$\underline{H}_2$), 1.7 (1H, brs, O$\underline{H}$), 1.2–1.1 (3H, t, C$\underline{H}_3$)

5-Methanesulphonyl-1-(2-cyclohexyl-2-acetoxyethylideneamino)-3-ethylhexahydrocyclopenta[d]imidazole-2(1H)-one $^1$H NMR (CDCl$_3$, δ): 7.4 (1H, d, C$\underline{H}$=N), 5.4–5.2 (1H, m, C$\underline{H}$OMs), 5.2–5.1 (1H, t, C$\underline{H}$OAc), 4.5–4.2 (2H, m, NC$\underline{H}$C$\underline{H}$N), 3.8–3.5 (1H, sextet, C$\underline{H}_2$N*), 3.3–3.0 (1H, sextet, C$\underline{H}_2$N*), 2.9 (3H, s, OSO$_2$C$\underline{H}_3$), 2.6–1.9 (4H, m, 2×C$\underline{H}_2$), 2.1 (3H, s, C$\underline{H}_3$CO$_2$), 1.8–1.5 (11H, m, remaining C$\underline{H}_2$'s), 1.2–1.1 (3$\underline{H}$, t, C$\underline{H}_3$CH$_2$)

EXAMPLE 5

5-(3-Carboxypropylthio)-1-(2-cyclohexyl-2-hydroxyethylideneamino)-3-ethylhexahydrocyclopenta[d]imidazol-2(1H)-one Following the general procedure of Example 2, this compound was prepared from the compound of Example 4.

$^1$H NMR (CDCl$_3$, δ): 7.2 (1H, d, CH=N), 5.3–4.4 (2H, brs, CO$_2$H and O$\underline{H}$), 4.4–4.2 (2H, m, NCHCHN), 4.2–4.1 (1H, t, $\underline{C}$HOH), 3.7–3.4 (1H, m, C$\underline{H}_2$N*), 3.3–3.0 (2H, m, C$\underline{H}_2$N* and SC$\underline{H}$), 2.7–2.4 (4H, m, C$\underline{H}_2$CO$_2$ and SC$\underline{H}_2$), 2.4–1.1 (17H, m, remaining C$\underline{H}_2$'s) overlain by 1.2–1.1 (3H, t, C$\underline{H}_3$)

EXAMPLE 6

5-(3-Carboxypropylthio)-1-(2-cyclohexyl-2-hydroxyethylamino)-3-ethylhexahydrocyclopenta[d]imidazol-2-(1H)-one $^1$H NMR (CDCl$_3$, δ): 6.1–4.5 (3H, brs, exchangeable protons), 4.2–4.0 (2H, m, NCHCHN), 3.6–2.9 (6H, m, C$\underline{H}_2$N, C$\underline{H}_2$NH, OC$\underline{H}$ and SC$\underline{H}$), 2.8–2.0 (4H, m, C$\underline{H}_2$CO$_2$ and CH$_2$S), 2.0–0.9 (17$\underline{H}$, m, remaining CH$_2$'s) overlain by 1.2–1.1 (3H, t, C$\underline{H}_3$)

EXAMPLE 7

5-(3-Carboxypropylthio)-1-(2-cyclohexyl-2-hydroxyethylideneamino)-3-methylhexahydrocyclopenta[d]imidazol-2(1H)-one This compound was prepared following the general procedure of Examples 1 and 2. The structure was confirmed by $^1$H NMR analysis (CDCl$_3$, δ): 7.2 (1H, d, N=C$\underline{H}$), 2.85 (3H, s, C$\underline{H}_3$).

EXAMPLE 8

5-(3-Carboxypropylthio)-1-(2-cyclohexyl-2-hydroxyethylamino)-3-methylhexahydrocyclopenta[d-]imidazol-2(1H)-one This compound was prepared from the compound of Example 7 following the general procedure of Example 3. The structure was confirmed by $^1$H NMR analysis (CDCl$_3$, δ): 2.8 (3H, s, C$\underline{H}_3$).

EXAMPLE 9

5-(3-Carboxypropylthio)-1-(2-cyclohexyl-2-hydroxyethylideneamino)-3-isopropylhexahydrocyclopenta[d]imidazol-2(1H)-one This compound was prepared following the general procedure of Examples 1 and 2. The structure was confirmed by $^1$H NMR analysis (CDCl$_3$, δ): 7.0 (1H, m, N=C$\underline{H}$), 1.2 (6H, m, Me$_2$CHN).

EXAMPLE 10

5-(3-Carboxypropylthio)-1-(2-cyclohexyl-2-hydroxyethylamino)-3-isopropylhexahydrocyclopenta[d]imidazol-2-(1H)-one This compound was prepared from the compound of Example 9 following the general procedure of Example 3. The structure was confirmed by $^1$H NMR analysis (CDCl$_3$, δ): 4.1 (2H, m, 2×CHN), 3.95 (1H, m, Me$_2$CHN), 1.2 (6H, dd, Me$_2$CHN).

EXAMPLE 11

5-(3-Carboxypropylthio)-1-(2-cyclohexyl-2-hydroxyethylideneamino)-3-cyclopropylhexahydrocyclopenta[d]imidazol-2(1H)-one This compound was prepared following the general procedure of Examples 1 and 2. The structure was confirmed by $^1$H NMR analysis (CDCl$_3$, δ): 7.3 (1H, d, N=CH), 4.3 (1H, m, CHN), 4.1 (2H, m, CHN and NCHCH$_2$CH$_2$), 3.2 (1H, m, OCH).

EXAMPLE 12

5-(3-Carboxypropylthio)-1-(2-cyclohexyl-2-hydroxyethylamino)-3-cyclopropylhexahydrocyclopenta[d]imidazol-2(1H)-one This compound was prepared from the compound of Example 11 following the general procedure of Example 3. The structure was confirmed by $^1$H NMR analysis (CDCl$_3$, δ): 4.0 (3H, m, 2×CHN and NCHCH$_2$CH$_2$), 0.8 (4H, m, NCHCH$_2$CH$_2$).

EXAMPLE 13

5-(3-Carboxypropylthio)-1-(2-cyclohexyl-2-hydroxyethylideneamino)hexahydrocyclopenta[d]imidazol-2(1H)-one This compound was prepared following the general procedure of Examples 1 and 2. The structure was confirmed by $^1$H NMR analysis (CDCl$_3$, δ): 7.1 (1H, d, N=CH), 4.4 (1H, t, CHN), 4.2 (1H, m, CHN), 4.1 (1H, t, OCH).

EXAMPLE 14

5-(3-Carboxypropylthio)-1-(2-cyclohexyl-2-hydroxyethylamino)hexahydrocyclopenta[d]imidazol-2(1H)one This compound was prepared from the compound of Example 13 following the general procedure of Example 3. The structure was confirmed by $^1$H NMR analysis (CDCl$_3$, δ): 4.2 (2H, m, 2×CHN), 3.2 (1H, m, OCH).

PHARMACEUTICAL FORMULATION EXAMPLES

The "active ingredient" in the following formulations is any compound of the invention (as hereinbefore defined, for example, any of the compounds of Synthetic Examples 1 to 14).

EXAMPLE A

Tablet

|  | Per tablet |
|---|---|
| Active Ingredient | 5.0 mg |
| Latose | 82.0 mg |
| Starch | 10.0 mg |
| Povidone | 2.0 mg |
| Magnesium Stearate | 1.0 mg |

Mix together the active ingredient, lactose and starch. Granulate the powders using a solution of povidone in purified water. Dry the granules, add the magnesium stearate and compress to produce tablets (100 mg per tablet).

EXAMPLE B

Ointment

| Active Ingredient | | 1.0 g |
|---|---|---|
| White Soft Paraffin | to | 100.0 g |

Disperse the active ingredient in a small volume of the vehicle. Gradually incorporate this into the bulk to produce a smooth, homogeneous product. Fill into collapsible metal tubes.

EXAMPLE C

Cream for topical use

| Active Ingredient | | 1.0 g |
|---|---|---|
| Polawax GP 200 | | 20.0 g |
| Lanolin Anhydrous | | 2.0 g |
| White Beeswax | | 2.5 g |
| Methyl hydroxybenzoate | | 0.1 g |
| Distilled Water | to | 100.0 g |

Heat the Polawax, beeswax and lanolin together at 60° C. Add a solution of methyl hydroxybenzoate. Homogenise using high speed stirring. Allow the temperature to fall to 50° C. Add and disperse the active ingredient. Allow to cool with slow speed stirring.

EXAMPLE D

Lotion for topical use

| Active Ingredient | | 1.0 g |
|---|---|---|
| Sorbitan Monolaurate | | 0.6 g |
| Polysorbate 20 | | 0.6 g |
| Cetostearyl Alcohol | | 1.2 g |
| Glycerin | | 6.0 g |
| Methyl Hydroxybenzoate | | 0.2 g |
| Purified Water B.P. | to | 100 ml |

The methyl hydroxybenzoate and glycerin were dissolved in 70 ml of the water at 75° C. The sorbitan monolaurate, Polysorbate 20 and cetostearyl alcohol were melted together at 75° C. and added to the aqueous solution. The resulting emulsion was homogenised, allowed to cool with continuous stirring and the active ingredient added as a suspension in the remaining water. The whole was stirred until homogeneous.

EXAMPLE E

Eye drops

| Active Ingredient | | 0.5 g |
|---|---|---|
| Methyl Hydroxybenzoate | | 0.01 g |
| Propyl Hydroxybenzoate | | 0.04 g |
| Purified Water B.P. | to | 100 ml |

The methyl and propyl hydroxybenzoates were dissolved in 70 ml of purified water at 75° C. and the resulting solution allowed to cool. The active ingredient was then added and the solution made up to 100 ml with purified water. The solution was sterilised by filtration through a membrane filter of 0.22 μm pore size and packed aseptically into suitable sterile containers.

EXAMPLE F

Injectable solution

| Active Ingredient | 10.0 mg |
| --- | --- |
| Water for Injections B.P. | to 1.0 ml |

The active ingredient was dissolved in half of the Water for Injections and then made up to volume and sterilised by filtration. The resulting solution was distributed into ampoules under aseptic conditions.

EXAMPLE G

Powder capsules for inhalation

| Active Ingredient (0.5–7.0 μm powder) | 4 mg |
| --- | --- |
| Lactose (30–90 μm powder) | 46.0 mg |

The powders were mixed until homogeneous and filled into suitably sized hard gelatin capsules (50 mg per capsule).

EXAMPLE H

Inhalation aerosol

| Active Ingredient (0.5–7.0 μm powder) | 200 mg |
| --- | --- |
| Sorbitan Trioleate | 100 mg |
| Saccharin Sodium (0.5–7.0 μm powder) | 5 mg |
| Methanol | 2 mg |
| Trichlorofluoromethane | 4.2 g |
| Dichlorodifluoromethane | to 10.0 ml |

The sorbitan trioleate and menthol were dissolved in the trichlorofluoromethane. The saccharin sodium and active ingredient were dispersed in the mixture which was then transferred to a suitable aerosol canister and the dichlorodifluoromethane injected through the valve system. This composition provides 2 mg of active ingredient in each 100 μl dose.

BIOLOGICAL ASSAY for inhibition of platelet aggregation

The average intrinsic activities (% of maximum possible response) and efficacies of a series of 10-substituted bicyclic analogues were obtained in the human washed platelet (inhibition of aggregation induced by $5 \times 10^{-5}$M ADP) and rabbit jugular vein (relaxation of tone induced by $1 \times 10^{-6}$M histamine). Numbers in brackets indicate numbers of replicates.

| COMPOUND EXAMPLE NO. | CALCULATED AVERAGE INTRINSIC ACTIVITY (%) | | EFFICACY RELATIVE TO SYNTHETIC EXAMPLE 14 | |
| --- | --- | --- | --- | --- |
| | Platelet (v. ADP $5 \times 10^{-5}$ M) | Jugular (v. Histamine $1 \times 10^{-6}$ M) | Platelet (calculated) | Jugular |
| 8 | 79 (4) | 52 (6) | 0.25 | 0.27 |
| 7 | 65 (4) | 31 (5) | 0.12 | 0.16 |
| 6 | 78 (6) | 41 (6) | 0.24 | 0.21 |
| 5 | 51 (5) | 16 (3) | 0.07 | 0.09 |
| 3 | 27 (5) | 9 (2) | 0.02 | 0.05 |
| 2 | 7 | 0 | 0.005 | — |

BIOLOGICAL ASSAY for reduction of intraocular pressure (IOP)

(i) Rabbits

Normotensive male rabbits weighing about 3 kg were used. Eye drops of the compound of Synthetic Example 14 (200 μg/ml and 1 mg/ml) were prepared as solutions in a mixture of glycerin and Tween 80 and applied topically (0.05 ml) to unilateral eyes. The contralateral eyes were untreated. IOP was measured at $t_0$ and 1, 2, 4, 6 and 8 hours after application with a Pneumatic Tonometer (Alcon). Data was obtained as ΔIOP (treated eye's IOP—untreated eye's IOP) and analysed statistically by the method of Dunnett.

The compound significantly reduced IOP at both concentrations for periods of 6 hours (200 μg/ml) and 8 hours (1 mg/ml). The IOP of the untreated eye was unaffected.

(ii) Cats

Normotensive male cats weighing about 4 kg were used. Eye drops of the compound of Synthetic Example 14 (40 μg/ml, 200 μg/ml and 1 mg/ml) were prepared as solutions in a mixture of glycerin and Tween 80 and applied topically (0.05 ml) to both eyes. IOP was measured as described above and the data analysed statistically by the method of Dunnett.

The compound significantly reduced IOP at all three concentrations for periods of 2 hours (40 μg/ml), 5 hours (200 μg/ml) and 7 hours (1 mg/ml).

TOXICITY

The compound of Synthetic Example 5 was administered to Wistar rats once daily for 14 days by slow bolus intravenous injection at dose levels of 0.1, 1.0 and 10 mg/kg/day. Serial blood samples were taken during the dosing phase. All animals were subjected to full macroscopic examination at necropsy and a comprehensive selection of tissues evaluated histopathologically.

No toxicologically significant effects were observed in the blood sample nor were any gross abnormalities or toxicologically meaningful effects on organ weights noted at autopsy. No evidence of any toxicologically significant effect was observed in the histopathological examination of the tissues.

We claim:

1. A compound of the formula:

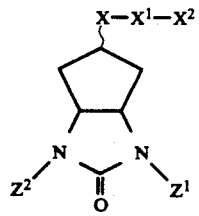

wherein

X is a sulfur atom or oxygen atom or a group —NR$^1$— or —CR$^1$R$^2$—, in the alpha- or beta-configuration, where R$^1$ and R$^2$ are hydrogen or straight or branched C$_{1-5}$ alkyl;

X$^1$ is a C$_{1-5}$ straight chain or branched alkylene group, a C$_{3-5}$ straight chain or branched alkenylene group or a substituted or unsubstituted C$_6$ or C$_{10}$ aromatic group, the optional substituents on the aromatic group being one or more of C$_{1-4}$ alkyl, C$_{1-4}$ alkoxy, nitro, halo and trihalomethyl;

$X^2$ is a cyano, carboxyl, carboxamide, hydroxymethyl, $C_{2-5}$ alkoxycarbonyl, or 5-tetrazolyl group;

$Z^1$ is a group selected from $-NH-CH_2-R^3$ and $-N=CH-R^3$ wherein $R^3$ is a group selected from $-CO-Y$ and $-CH(Y^1)Y$, Y being a group selected from $C_{3-8}$ alkyl, $C_{3-8}$ alkenyl, phenyl-$C_{1-4}$ alkyl and phenyl, wherein the phenyl group in both cases is optionally substituted by one or more groups independently selected from $C_{1-4}$ alkyl, $C_{1-4}$ alkoxy, nitro, halo and trihalomethyl, cycloalkyl of from 4 to 8 carbon atoms and $Y^1$ being a group selected from hydroxy, hydrogen, $C_{1-4}$ alkoxy and $C_{1-5}$ alkanoyloxy;

$Z^2$ is hydrogen, a $C_{1-12}$ straight or branched alkyl, $C_{2-12}$ alkenyl or alkynyl, $C_6$ or $C_{10}$ aryl or $C_6$ or $C_{10}$ aryl-$C_{1-12}$ alkyl wherein the aryl group is optionally substituted by one or more groups independently selected from phenyl, $C_{1-4}$ alkyl, $C_{1-4}$ alkoxy, nitro, halo and trihalomethyl, or cycloalkyl of from 3 to 5 carbon atoms;

or a salt or an ester thereof.

2. The compound of claim 1 wherein:

X is a sulfur atom, an oxygen atom or a methylene group in the beta-configuration;

$X^1$ is a $C_{3-4}$ straight alkyl chain;

$X^2$ is a carboxy group or a corresponding $C_{1-4}$ alkyl ester or salt thereof;

$Z^1$ is a group selected from $-NH-CH_2-R$, where R is a group of the formula $-CH(Y^1)Y$ in which $Y^1$ is hydroxy and Y is phenyl, alkyl of 3 to 8 carbon atoms, or cycloalkyl of 4 to 8 carbon atoms; and $Z^2$ is a group selected from hydrogen, $C_{1-6}$ straight and branched alkyl and $C_3$-$C_6$ cycloalkyl or a salt or an ester thereof.

3. 5-(3-Carboxypropylthio)-1-(2-cyclohexyl-2-hydroxyethylamino)-hexahydrocyclopenta[d]imidazol-2(1H)-one or a salt or an ester thereof.

4. 5-(3-Carboxypropylthio)-1-(2-cyclohexyl-2-hydroxyethylideneamino)-hexahydrocyclopenta[d]imidazol-2(1H)-one or a salt or an ester thereof.

5. A pharmaceutical composition comprising a therapeutically effective amount of a compound of claim 1 and a pharmaceutical carrier.

6. The pharmaceutical composition of claim 5 in a form suitable for oral, buccal, parenteral, rectal, or topical administration.

7. A method for preventing or treating a thromboembolic disorder in a mammal which comprises administering to said mammal a therapeutically effective amount of a compound of claim 1.

8. A method for preventing or treating a condition giving rise to increased intraocular pressure in a mammal which comprises administering to said mammal a therapeutically effective amount of a compound of claim 1.

9. The method according to claim 8 wherein said condition is glaucoma.

* * * * *